(12) United States Patent
Charpillat

(10) Patent No.: US 6,382,834 B2
(45) Date of Patent: May 7, 2002

(54) BELT TENSIONER AND A RADIOLOGY APPARATUS EQUIPPED WITH SUCH A BELT

(75) Inventor: Bernard Charpillat, Nerville la Foret (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/847,547

(22) Filed: May 2, 2001

(30) Foreign Application Priority Data

May 9, 2000 (FR) .............................. 00 05892

(51) Int. Cl.⁷ ................................................ H05G 1/02
(52) U.S. Cl. ............................ 378/197; 474/110; 474/5
(58) Field of Search ........................ 378/197; 474/110, 474/133, 5

(56) References Cited

U.S. PATENT DOCUMENTS

| 4,064,500 A | | 12/1977 | Sokol ..................... 340/267 R |
| 4,355,991 A | * | 10/1982 | Kraft ......................... 474/110 |
| 4,571,223 A | * | 2/1986 | Molloy ....................... 474/133 |
| 5,048,069 A | | 9/1991 | Siczek ......................... 378/197 |
| 5,982,844 A | * | 11/1999 | Tybinkowski et al. ......... 378/4 |
| 6,151,924 A | * | 11/2000 | Plath et al. ................ 66/132 T |
| 6,337,894 B1 | * | 1/2002 | Tybinkowski et al. ......... 378/4 |

FOREIGN PATENT DOCUMENTS

| FR | 2621166 | 3/1989 | ............ H01B/7/32 |
| JP | 62167962 | 7/1987 | ............ F16H/7/00 |

OTHER PUBLICATIONS

Patent Abstracts of Japan, vol. 012, No. 004 (M–657) Jan. 8, 1988.

* cited by examiner

Primary Examiner—David V. Bruce
Assistant Examiner—Irakli Kiknadze
(74) Attorney, Agent, or Firm—Jay L. Chaskin

(57) ABSTRACT

Belt tensioner comprising a support, a roller designed to be in contact with the belt to be tensioned, a roller carrier on which the roller is mounted rotationally and which is mounted on the support so as to move back and forth between two extreme positions, a spring arranged between the support and the roller carrier in such a way as to urge the roller carrier continuously from a first to a second of the two extreme positions, a two-way switch mounted on the support in such a way as to be actuated by the roller carrier to occupy a first state only when the roller carrier is at the first extreme position and to pass into the second state when the roller carrier has left this first extreme position under the action of the spring, and means for mounting the support on a base so that the roller carrier occupies the first extreme position only when the belt is intact and has a predetermined tension.

27 Claims, 3 Drawing Sheets

BELT TENSIONER AND A RADIOLOGY APPARATUS EQUIPPED WITH SUCH A BELT

CROSS REFERENCE TO RELATED APPLICATIONS

This application claims the benefit of a priority under 35 USC 119 to French Patent Application No. 0005892 filed May 9, 2000, the entire contents of which are incorporated by reference.

BACKGROUND OF THE INVENTION

The present invention relates to a belt tensioner having means for protecting against rupture or loosening or relaxation or breakage or stretching or layer separation or tooth tearing of the belt. Each of these belt conditions is an example of belt failure. In particular the present invention relates to a belt having an integrated safety device to protect belt failure.

Transmission or drive belts are used, for example, between a motor and the system driven by such motor when a direct drive proves to be impossible, for example for reasons of space, present problems of reliability. Systematic replacement of such belts after a predetermined period of operation only partially remedies these problems.

In some applications, from the viewpoint of safety, it is absolutely essential to prevent the consequences of such a failure of a transmission or drive belt. This is the case, for example, with a radiology apparatus such as a x-ray apparatus that may comprise a mobile or movable piece of equipment situated above the patient. The raising and lowering of the equipment may be controlled by means of a transmission or drive belt, where failure of the belt may cause falling of the mobile or movable equipment if the failure is not substantially instantaneously detected, with immediate and priority locking of the mobile or movable equipment.

BRIEF DESCRIPTION OF THE INVENTION

In an embodiment of the present invention a belt tensioner comprises an integrated safety device substantially instantaneously detecting failure of the belt such that this information may be transmitted, for example, for the immediate and priority intervention to prevent any untoward consequence of such a failure.

In addition, an embodiment of the invention is a radiology apparatus, such as a x-ray apparatus, equipped with such a belt tensioner.

The belt tensioner in an embodiment of the invention comprises: a means for support; a roller; a means for carrying on which the roller is mounted for rotation and which is mounted on the support so that it can move back-and-forth between two extreme positions, means for urging the means for carrying from a first to a second of the two extreme positions, the means for urging being arranged between the support and the means for carrying, means for actuation by the means for carrying so as to occupy a first state only when the means for carrying is at the first extreme position and to switch to the second state as soon as or when the means for carrying has left this first extreme position under the action of the means for urging, the means for actuation being mounted on the support, and means for mounting the support on a base, in a fixed position in relation to the belt to be tensioned, so that the means for carrying occupies the first extreme position only when the belt is intact and has a predetermined tension.

BRIEF DESCRIPTION OF THE DRAWINGS

An illustrative and non-limitative embodiment of a belt tensioner will be described below in greater detail with reference to the accompanying schematic drawings, wherein.

DETAILED DESCRIPTION OF THE INVENTION

Figure 1:
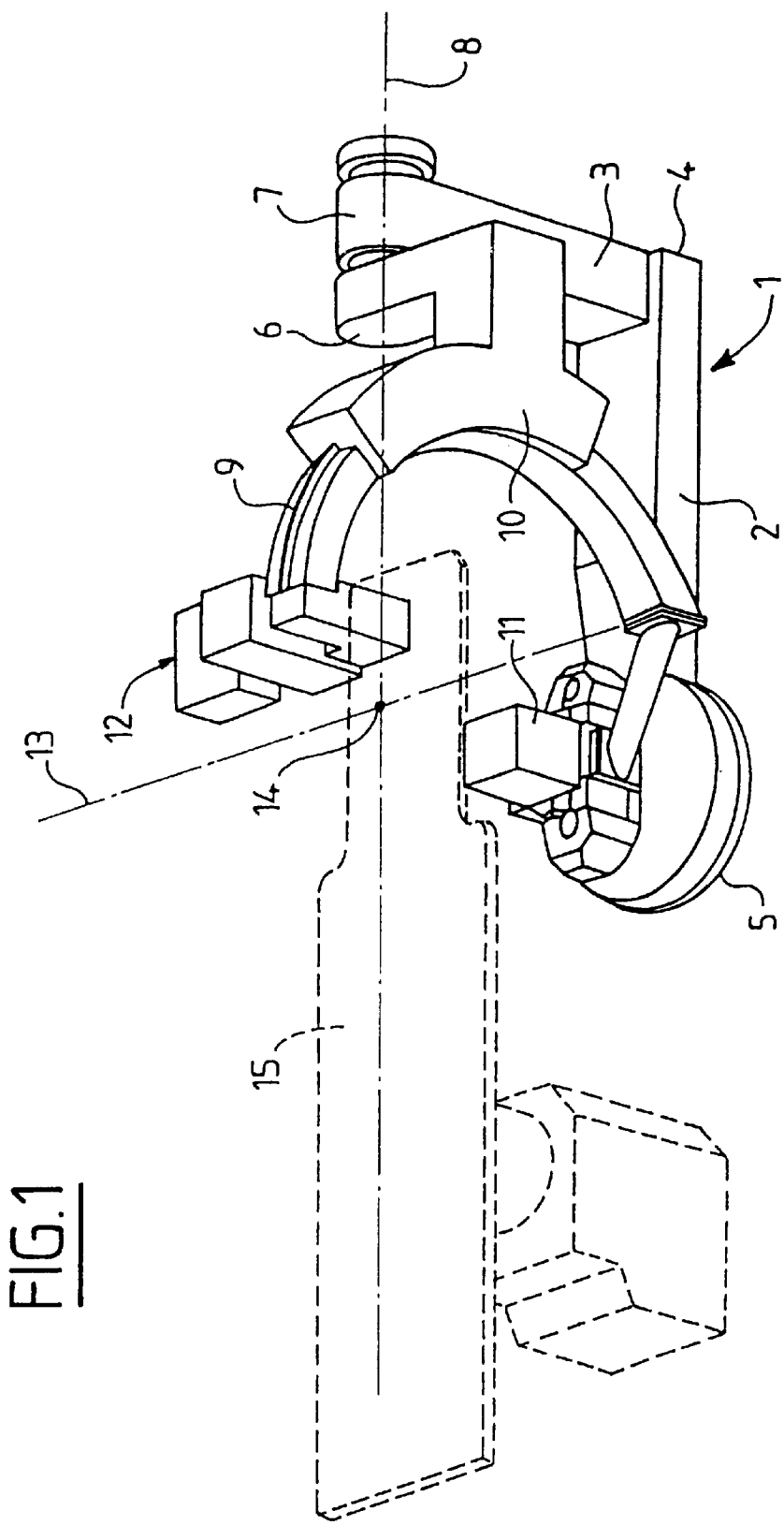
FIG. 1 is a perspective view of a radiology apparatus.

As illustrated by FIG. 1, a radiology apparatus comprises an L-shaped stand 1, with a substantially horizontal base 2 and a substantially vertical upright 3 at one end 4 of the base 2. At the opposite end 5, the base 2 comprises an axis of rotation parallel to the upright 3, about which the stand 1 can rotate. A first end of a supporting arm 6 is mounted on the top 7 of the upright 3, so as to be able to rotate on a horizontal axis 8. The supporting arm may have the shape of a bayonet. An arm 9, in the shape of an arc of a circle (C-shaped), is held at the other end 10 of the supporting arm 6. The C-shaped arm 9 is capable of sliding in rotational motion about an axis 13, with respect to the end 10 of the supporting arm 6.

The C-shaped arm 9 bears a tube 11, which provides a beam source of radiation, typically x-rays, and a detector 12 for such radiation in diametrically opposed facing positions. The detector 12 comprises a plane detection surface. The direction of the radiation beam is determined by a straight line joining a focal point of the tube 11 at the center of the plane surface of the detector 12. The three axes of rotation of the stand 1, of the supporting arm 6 and of the C-shaped arm 9 are secants at a point 14. In middle position, these three axes are mutually perpendicular.

A table 15, provided for accommodating an object or patient, has a longitudinal orientation aligned with the axis 8 in rest position. The table 15, motorized or not, can be moved in translation along a plurality of axes.

In some cases, the detector 12 should be capable of being adjusted (in height) with relation to the patient lying on the table 15. This is the reason why the detector 12 should be mobile or movable (in height) with respect to the C-shaped arm 9 which carries the detector.

Figure 2:
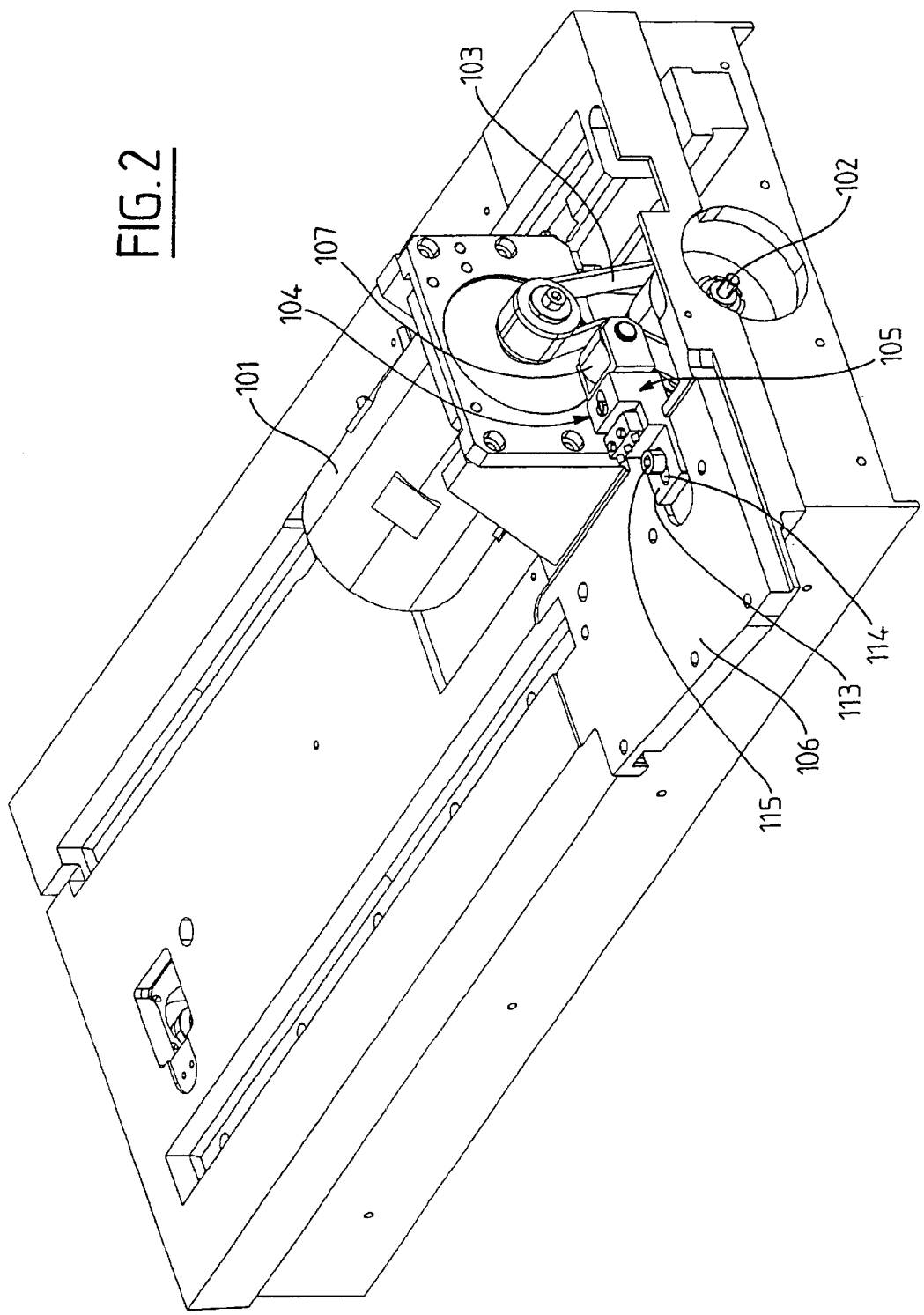
FIG. 2 is a perspective view showing an example of installation of a belt tensioner according to an embodiment of the invention.

According to FIG. 2, the movement of the detector 12 is controlled by a motor 101, connected to a driven element 102 by a transmission that comprises a belt 103, for example, a flat belt or a toothed belt. A tension device 104 is associated with the belt 103, to ensure correct tension of the belt.

Figure 3:
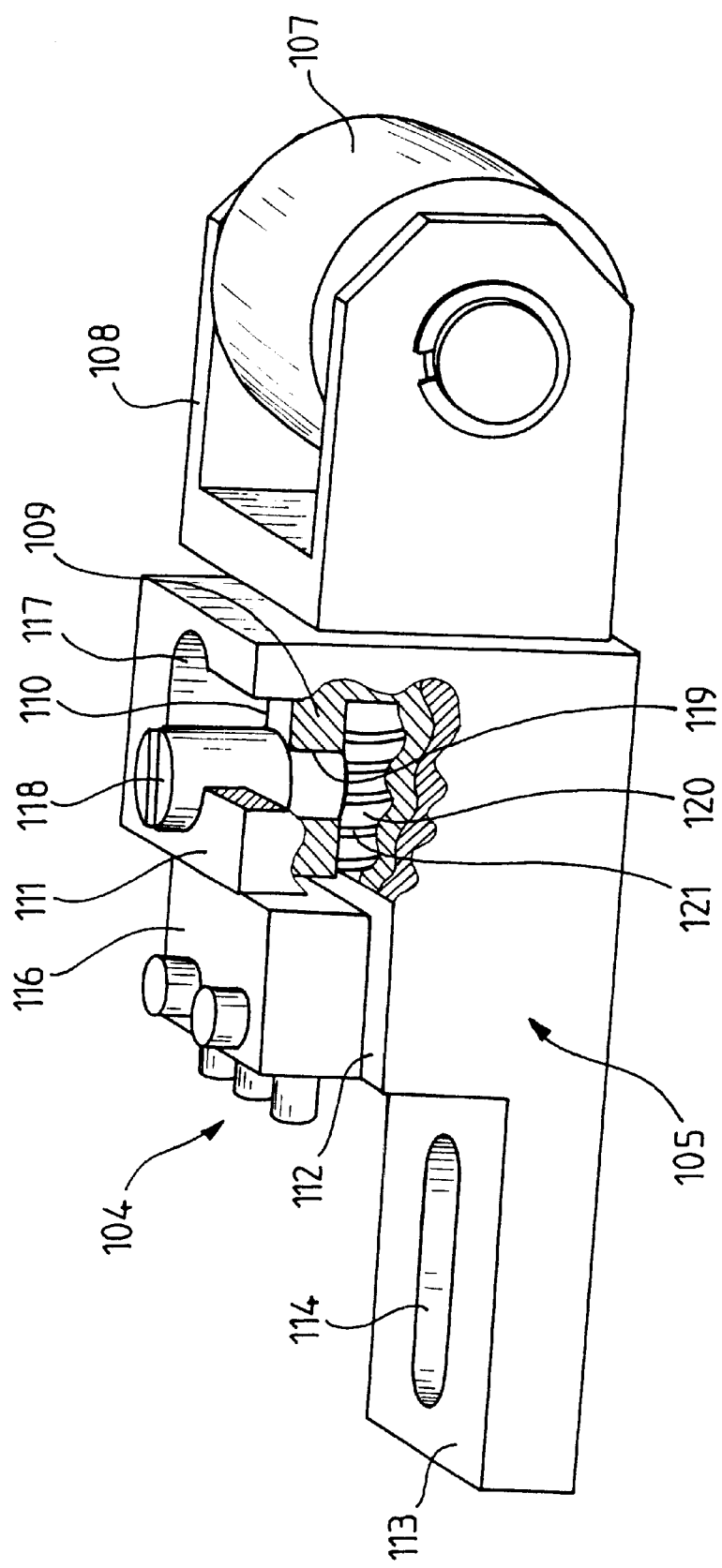
FIG. 3 is a perspective view showing the structure of the belt tensioner of FIG. 2.

The tension device 104, whose structure appears more clearly in FIG. 3, comprises an elongated support 105, fixed on the same base 106 as the motor 101, and a roller 107 mounted on means for carrying so that it can rotate in comprising a clevis 108 having a cylindrical end piece 109 mounted to be movable in longitudinal translation in a cylindrical housing 110 provided in the support 105. The support 105, in its upper part, has a stepped shape, comprising, starting from the end of the piece 109 of the clevis 108 in the housing 110, a high step 111, a middle step 112 and a low step 113.

Step 113 is traversed by a longitudinal vertical slot 114 that permits, by means of a screw 115, fixation of the tension device 110 on or to the base 106, with the possibility of adjustment of the position of the tension device 104 with respect to the belt 103. Step 112 carries means for actuation comprising a two-way switch 116, whose switching element, not represented, is turned toward or faces the step 111. The housing 110 traverses the step 111, its upper part opening opposite the actuating element of the switch 116. Step 111 is in addition traversed from the top down to the housing 110 by a vertical longitudinal slot 117, shorter in length than the length of the step 111. Slot 117 serves as a guide for a screw 118 engaged from the top, through the slot 117, in a transverse hole 119 of the end piece 109, the screw 118, in cooperation with the slot 117, preventing rotation of the end piece 109 and hence of the clevis 108, and limiting longitudinal movement of the clevis 108 and hence of the roller 107.

A blind hole 120 is provided in the end piece 109, starting the free end of the end piece. The hole 120 contains a means for urging comprising a compression spring 121 that is compressed on one side between the bottom of the hole 120 and the end wall that closes the housing 110 in the lower part of the latter (to the level of the step 112). Above the step 112, the housing 110 does not have an end wall, which permits the free end of the piece 109 to act on the actuating element of the switch 116 when the piece 109 occupies the position according to FIG. 2, in which it is completely set into the housing 110, the screw 118 bearing on the left end of the slot 117. It is in this position, in which the spring 121 is compressed to the maximum under the effect of the tension of the belt 103, that the switch 116 is actuated by the piece 109. The spring 121 is chosen so that the maximum force that the spring exerts on the piece 109 in the extreme position defined by abutment of the screw 118 against the left end of the slot 117 corresponds to the desired tension of the belt 103.

When the tensioner 104 has been mounted on the base 106, the roller 107 being in contact with the belt, the support 105 is pushed in the direction of the belt 103, increasing the tension of the latter, until screw 118, which at the beginning was applied under the action of the spring 121 against the right-hand end of the slot 117, is displaced in and along this slot until it comes into abutment against the left-hand end (the position shown in FIG. 3), the piece 109 thus actuating the switch 116. It is in this position that the support 105 is locked on the base 106 by means of the screw 115.

The switch 116 preferably is mounted so that it is in the closed state in this position of the roller carrier, composed of the clevis 108 and of the end piece 109, and switches to the open state as soon as the roller carrier 108, 109 leaves this position, following failure of the belt 103.

The switch 116 thus substantially instantaneously signals, for example to the control system of the radiology apparatus, any failure of the belt 103, the control system thus being able immediately to ensure, as a matter of priority, locking of the detector 12, and therefore to prevent any inadvertent lowering of the detector 12 in the direction of the patient.

Preferably, the means for mounting is designed in such a way that the support can be mounted on the base such that its position can be adjusted in relation to the belt.

The means for mounting may comprise at least one slot extending into the support parallel to the direction of movement of the carrier, and at least one locking screw traversing the slot to lock the support to the base.

The switch preferably is mounted so that it is in the closed state when the means for carrying occupies the first extreme position. Thus, the belt tension system is self-checking and thus ensures safety in that failure of the belt is reflected in opening of the switch, any failure of the switch being interpreted as a failure of the belt. This solution offers the best safety for the lowest cost.

It should be noted that the belt tensioner according to an embodiment of the invention may have multiple applications other than for a radiology apparatus.

In addition, the structure or function of the belt tensioner has been described above only by way of an illustrative and non-limitative example, the invention covering any and all modifications and variants, provided that the tensioner retains its essential functions as defined above.

Various modifications in structure and/or steps and/or function may be made by one skilled in the art without departing from the scope of the invention.

What is claimed is:

1. A tensioner for a belt comprising:
   (a) a support;
   (b) a roller in contact with the belt;
   (c) means for rotationally carrying the roller, the means for carrying being mounted on the support to permit back-and-forth motion between two extreme positions;
   (d) means for urging the means for carrying from a first to a second of the two extreme positions, the means for urging arranged between the support and the means for carrying;
   (e) means for switching to cause the means for carrying to occupy a first state only when the means for carrying is at the first extreme position and to pass into the second state when the means for carrying has left this first extreme position under the action of the means for urging;
   (f) means for mounting the support on a base so that the means for carrying occupies the first extreme position only when the belt is intact and has a predetermined tension;
   (g) the roller being mounted in a clevis having an extension mounted movable in longitudinal translation in the support; and
   a free end of the extension acting on the means for switching for operating the means for switching.

2. The tensioner according to claim 1, wherein the means for mounting allows the support to be mounted on the base so as to be adjustable in position with relation to the belt.

3. The tensioner of claim 2 wherein:
   (i) a housing open at its bottom opposite to the switch for operating the switch by the free end of the extension.

4. The tensioner of claim 2 wherein:
   (i) the extension of the clevis is a cylindrical extension mounted movable in longitudinal translation in a cylindrical housing of the support; and
   (j) the support is provided with a longitudinal slot acting as a guide for a screw engaged through the slot into a transverse hole in the extension for preventing the clevis from rotating and limiting the longitudinal excursion of the clevis.

5. The tensioner of claim 4 wherein:
   the spring is a compression spring compressed between the means for rotationally carrying the roller and the support.

6. The tensioner according to claim 1, wherein means for mounting comprises a slot extending into the support parallel to the direction of mobility of the means for carrying and at least one means for locking traversing the slot to lock the support on the base.

7. The tensioner of claim 6 wherein:

the support has a plurality of steps, the lowest step being located at the slot.

8. The tensioner according claim 1 wherein the means for switching is mounted in such a way that it is in the closed state when the means for carrying occupies the first extreme position.

9. The tensioner according to claim 1 wherein:
(i) the extension of the clevis is a cylindrical extension mounted movable in longitudinal translation in a cylindrical housing of the support; and
(j) the support is provided with a longitudinal slot acting as a guide for a screw engaged through the slot into a transverse hole in the extension for preventing the clevis from rotating and limiting the longitudinal excursion of the clevis.

10. The machine of claim 9 wherein:
(i) a housing open at its bottom opposite to the switch for operating the switch by the free end of the extension.

11. The tensioner of claim 1 wherein:
(i) a housing open at its bottom opposite to the switch for operating the switch by the free end of the extension.

12. The tensioner of claim 1 wherein:
the spring is a compression spring compressed between the means for rotationally carrying the roller and the support.

13. The tensioner of claim 1 wherein:
the support has a plurality of steps, the highest step being adjacent to the extension.

14. A tensioner for a belt comprising:
(a) a support;
(c) a roller in contact with the belt to be tensioned;
(c) a roller carrier on which the roller is rotatably mounted and which is mounted on the support so that it moves back and forth between two extreme positions;
(d) a spring arranged between the support and the carrier to urge the roller carrier from a first to a second of the two extreme positions;
(e) a two-way switch mounted on the support so as to be actuated by the roller carrier to occupy a first state only when the roller carrier is at the first extreme position and to switch to the second as soon as the roller carrier has left the first extreme position under the action of the spring;
(f) means for mounting the support on a base wherein the roller carrier occupies the first extreme position only when the belt is intact and has a predetermined tension; and
(g) the roller being mounted in a clevis having an extension mounted movable in longitudinal translation in the support, and
(h) a free end of the extension acting on the means for switching for operating the means for switching.

15. The tensioner according to claim 14 wherein the means for mounting is designed so that the support can be mounted on the base such that its position can be adjusted with respect to the belt.

16. The tensioner according to claim 14 wherein the means for mounting comprises a slot extending into the support parallel to the direction of movement of the roller carrier and at least one locking screw traversing the slot to lock the support on the base.

17. The tensioner according to claim 16 wherein the switch is mounted wherein it is in the closed state when the roller carrier occupies the first extreme position.

18. The tensioner according to claim 14 wherein the switch is mounted wherein it is in the closed state when the roller carrier occupies the first extreme position.

19. The tensioner according to claim 15 wherein the switch is mounted wherein it is in the closed state when the roller carrier occupies the first extreme position.

20. The tensioner of claim 14 wherein:
the spring is compressed between a bottom of a blind hole formed in the extension starting from the free end and the bottom of the housing.

21. Radiology machine comprising:
(d) a source of radiation;
(e) a detector of the radiation;
(c) means for adjusting the distance between the source of radiation and the detector, the adjusting means comprising:
(l) a belt tensioner comprising:
(a) a support;
(b) a roller in contact with a belt;
(c) means for rotationally carrying the roller, the means for carrying being mounted on the support to permit back-and-forth motion between two extreme positions;
(d) means for urging the means for carrying from a first to a second of the two extreme positions, the means for urging arranged between the support and the means for carrying;
(e) means for switching to cause the means for carrying to occupy a first state only when the carrying means is at the first extreme position and to pass into a second state when the means for carrying has left the first extreme position under the action of the means for urging;
(f) means for mounting the support on a base so that the means for carrying occupies the first extreme position only when the belt is intact and has a predetermined tension; and
(g) the roller being mounted in a clevis having an extension mounted movable in longitudinal translation in the support; and
(h) a free end of the extension acting on the means for switching for operating the means for switching.

22. The machine of claim 21 wherein:
(i) the extension of the clevis is a cylindrical extension mounted movable in longitudinal translation in a cylindrical housing of the support; and
(j) the support is provided with a longitudinal slot acting as a guide for a screw engaged through the slot into a transverse hole in the extension for preventing the clevis from rotating and limiting the longitudinal excursion of the clevis.

23. The machine of claim 22 wherein:
the support has a plurality of steps, the lowest step being located at the slot.

24. The machine of claim 21 wherein:
(i) a housing open at its bottom opposite to the switch for operating the switch by the free end of the extension.

25. The machine of claim 21 wherein:
the spring is a compression spring compressed between the means for rotationally carrying the roller and the support.

26. The machine of claim 21 wherein:
the spring is compressed between a bottom of a blind hole formed in the extension starting from the free end and the bottom of the housing.

27. The machine of claim 21 wherein:
the support has a plurality of steps, the highest step being adjacent to the extension.

* * * * *